United States Patent [19]
Gante et al.

[11] 4,115,456
[45] Sep. 19, 1978

[54] ALKYNE COMPOUNDS AND METHOD OF USE

[75] Inventors: Joachim Gante; Hans-Adolf Kurmeier; Dieter Orth; Erich Schacht; Albrecht Wild, all of Darmstadt, Fed. Rep. of Germany

[73] Assignee: Merck Patent Gesellschaft mit beschrankter Haftung, Darmstadt, Fed. Rep. of Germany

[21] Appl. No.: 697,579

[22] Filed: Jun. 18, 1976

[30] Foreign Application Priority Data

Jun. 19, 1975 [DE] Fed. Rep. of Germany ....... 2527352

[51] Int. Cl.$^2$ ............................................. C07C 43/20
[52] U.S. Cl. ................................ 260/613 R; 424/341; 424/345; 560/100; 560/107; 560/255; 568/807; 568/809
[58] Field of Search ....................... 260/618 E, 613 R; 424/341, 345

[56] References Cited

U.S. PATENT DOCUMENTS 3,879,449  4/1975  Anderson et al. ............... 260/618 E

FOREIGN PATENT DOCUMENTS 2,258,349  6/1973  Fed. Rep. of Germany ....... 260/618 E
1,307,360  2/1973  United Kingdom ............... 260/618 E Primary Examiner—Paul J. Killos
Attorney, Agent, or Firm—Millen & White

[57] ABSTRACT

Alkyne compounds of the formula

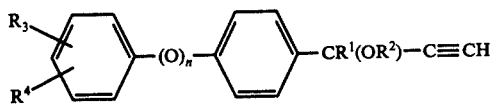

wherein $R^1$ is H, alkyl of up to 4 carbon atoms or phenyl; $R^2$ is H, aliphatic acyl of up to 6 carbon atoms or aroyl of up to 11 carbon atoms; $R^3$ and $R^4$ are H, F, Cl or Br and $n$ is 0 or 1, and physiologicaly acceptable metals salts thereof, have antiinflammatory activity. These compounds can be made from compounds of the formula

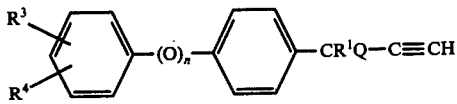

wherein Q is a functionally-modified hydroxy and $R^1$, $R^3$, $R^4$ and $n$ are as above by treatment with a solvolyzing agent.

24 Claims, No Drawings

ALKYNE COMPOUNDS AND METHOD OF USE

BACKGROUND OF THE INVENTION

This invention relates to novel 3-biphenylyl-3-hydroxyprop-1-yne and 3-aryloxyphenyl-3-hydroxyprop-1-yne compounds.

SUMMARY OF THE INVENTION

In a composition aspect, this invention relates to novel alkyne compounds of Formula I

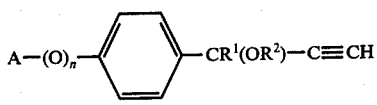

wherein $R^1$ is H, alkyl of up to 4 carbon atoms or phenyl; $R^2$ is H, alkanoyl of up to 6 carbon atoms or aroyl of up to 11 carbon atoms; A is

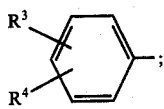

$R^3$ and $R^4$ are H, F, Cl or Br and $n$ is 0 or 1, and physiologically acceptable metal salts thereof.

In another compositional aspect, this invention relates to an anti-inflammatory pharmaceutical composition, comprising a compound of Formula I, in admixture with a pharmaceutically acceptable carrier.

In a method-of-use aspect, this invention relates to a method of treating an animal afflicted with an inflammatory condition, comprising administering to the afflicted animal an anti-inflammatorily effective amount of a compound of Formula I, in admixture with a pharmaceutically acceptable carrier.

In a process aspect, this invention relates to a process for preparing alkyne derivatives of Formula I and physiologically acceptable metal salts thereof, by treating a compound of Formula II

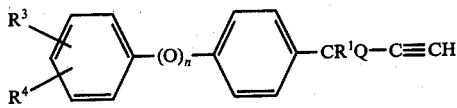

wherein Q is a functionally-modified hydroxyl group and $R^1$, $R^3$, $R^4$ and $n$ are as above with a solvolyzing agent and the further step of treating a resulting compound of Formula I ($R^2$ is H) with an acylating agent or converting a resulting compound Formula I with a base to a physiologically acceptable metal salt, or liberating a compound of Formula I from a salt thereof.

DETAILED DESCRIPTION $R^1$ can be H, ethyl, propyl, isopropyl, butyl, isobutyl, sec.-butyl or tert.-butyl, but $R^1$ is preferably methyl and $R^2$, when aliphatic acyl, is preferably alkanoyl of up to 6 carbon atoms, e.g., acetyl, propionyl, butyryl, pivaloyl, formyl, isobutyryl, pentanoyl, 2-methylbutyryl and hexanoyl.

When $R^2$ is aroyl, it preferably is the acyl radical of a mono or bicyclic carbocyclic acid of up to 11 carbon atoms, e.g., o-, m- or p-methylbenzoyl; o-, m- or p-fluorobenzoyl; o-, m- or p-chlorobenzoyl; naphthyl-1-carbonyl or naphthyl-2-carbonyl. Benzoyl is preferred. Also preferred for $R^2$ is H.

The terminal phenyl radical, which is substituted by $R^3$ and $R^4$ is designated A in Formula I above. A is preferably unsubstituted or mono-substituted phenyl or phenyl substituted by 2 fluorine. A single substituent is preferably in the p-position, but can be in the o-position or m-position. If A is disubstituted, $R^3$ and $R^4$ are preferably in the 2,4-position, but can be in the 2,3-, 2,5-, 2,6-, 3,4- or 3,5-position.

$R^3$ and $R^4$ can be the same or different. One of $R^3$ and $R^4$ is preferably H and the other is H, F or Cl. Compounds in which $R^3$ and $R^4$ each are F are also preferred.

A is preferably phenyl, o-, m- or, most preferably, p-fluorophenyl; o-, m- or, most preferably, p-chlorophenyl or 2,4-difluorophenyl. A can also be o-, m- or p-bromophenyl; 2,3-, 2,5-, 2,6-, 3,4- or 3,5-difluorophenyl; 2,3-, 2,5-, 2,6-, 3,4-, 3,5- or, preferably, 2,4-dichlorophenyl; chlorofluorophenyl, e.g., 2-chloro-3-, -4-, -5- or -6-fluorophenyl, 3-chloro-2-, -4-, or -5-fluorophenyl, 4-chloro-2- or -3-fluorophenyl or 5-chloro-2-fluorophenyl; dibromophenyl, such as 2,4-dibromophenyl; bromofluorophenyl, such as 2-bromo-4-fluorophenyl or 4-bromo-2-fluorophenyl; or bromochlorophenyl, such as 2-bromo-4-chlorophenyl or 4-bromo-2-chlorophenyl.

If $n$ is 1, $A\text{-}(O)_n\text{-}(p)\text{-}C_6H_4$ is preferably 4-(4-chlorophenoxy)phenyl. Otherwise, $n$ is preferably 0 and $A\text{-}(O)_n\text{-}(p)\text{-}C_6H_4$ is preferably 4-biphenylyl substituted or unsubstituted on the terminal phenyl group.

Preferred compounds of Formula I are those in which at least one of $R^1$, $R^2$, A, $R^3$, $R^4$ or $n$ is a preferred value. Preferred compounds of Formula I include those wherein:

(a) $n$ is 0;
(b) $n$ is 1; particularly those wherein $R^1$ is methyl and $R^3$ and $R^4$ are H;
(c) $R^2$ is H, including (a)-(b);
(d) $R^2$ is alkanoyl of up to 6 carbon atoms, including (a)-(b);
(e) $R^2$ is aroyl of up to 11 carbon atoms, including (a)-(b);
(f) A is phenyl, fluorophenyl or difluorophenyl, including (a)-(e);
(g) A is phenyl, o- or p-fluorophenyl or 2,4-difluorophenyl, including (a)-(e);
(h) A is phenyl, o- or p-fluorophenyl, p-chlorophenyl or 2,4-difluorophenyl; $R^1$ is methyl, $R^2$ is H and $n$ is 0;
(i) A is phenyl, o- or p-fluorophenyl, p-chlorophenyl or 2,4-difluorophenyl; $R^1$ is methyl; $R^2$ is alkanoyl of 2-5 carbon atoms or benzoyl and $n$ is 0;
(j) A is phenyl, o- or p-fluorophenyl, p-chlorophenyl or 2,4-difluorophenyl; $R^1$ is methyl, $R^2$ is H and $n$ is 1 and
(k) A is phenyl, o- or p-fluorophenyl, p-chlorophenyl or 2,4-difluorophenyl; $R^1$ is methyl; $R^2$ is alkanoyl of 2-5 carbon atoms or benzoyl and $n$ is 1.

Compounds of Formula I are prepared by known methods, such as described in standard reference works, e.g., Houben-Weyl, Methoden der Organischen Chemie (Methods of Organic Chemistry), Georg-Thieme-Verlag, Stuttgart, and Organic Reactions, John Wiley & Sons, Inc., New York, under the reaction conditions known to be suitable for the reaction of interest. It is also possible to use known variants, which are not described in more detail here.

Some of the starting materials for preparation of compounds of Formula I are known. New ones can be prepared by known processes. The starting materials can also be formed in situ so that they are not isolated from the reaction mixture but are immediately reacted further to give compounds of Formula I.

Compounds of Formula I are prepared by solvolysis, especially hydrolysis, of compounds of Formula II. Q is a functionally modified hydroxyl group, for example, metal alcoholate or acyloxy.

Preferably, Q is a metal alcoholate OM and M is one equivalent of a metal atom, for example, one equivalent of an alkali or alkaline earth metal atom, preferably Li, Na, K, Rb or Cs, or is one of MgHal, CaHal, SrHal or BaHal (Hal is Cl, Br or I). However, M can also be one equivalent of a heavy metal atom, for example, metals of groups Ib and IIb of the periodic table, as defined in Lange's "Handbook of Chemistry" (11th edition), including copper, zinc, cadmium or mercury.

Compounds of Formula II (Q is OM) are preferably prepared in situ. They can be obtained by reacting carbonyl compounds of formulae A—(p)—$C_6H_4$—CO—$R^1$ or A—O—(p)—$C_6H_4$—$COR^1$, wherein A and $R^1$ are as above, with metal acetylides.

The carbonyl compounds and alkali or alkaline earth metal acetylides, preferably NaC≡CH or LiC≡CH, as well as KC≡CH or Ca(C≡CH)$_2$, can be reacted in an inert solvent at temperatures between 0° and 100°, preferably at about 15°-50°.

Examples of inert solvents which can be used are open-chain lower ethers, such as diethyl, diisopropyl or diisobutyl ether; cyclic ethers, such as tetrahydrofuran (THF) of dioxane; lower acylamides, such as formamide or acetamide; lower dialkylacylamides, such as dimethylformamide (DMF), diethylformamide or dimethylacetamide; lower alkanal acetals, such as methylal; dimethyl sulfoxide (DMSO) and/or diethyl sulfoxide. An inert gas, such as $N_2$ or Ar, can be passed into the mixture during the reaction.

Diamine complexes of the alkali metal acetylides, for example, with ethylenediamine, preferably lithium acetylide/ethylenediamine complex, can also be used as alkynylating agent. This reaction is carried out using the solvents listed above, for example, THF, DMSO and/or dioxane, preferably at room temperature in the presence of an inert gas, such as $N_2$.

The reaction between carbonyl compounds and alkali or alkaline earth metal acetylides can also advantageously be carried out using agents which form acetylides from acetylene in situ under the indicated reaction conditions. Examples of such agents are alkali or alkaline earth metal amides, hydrides or enolates; alkali or alkaline earth metals themselves and organometallic alkali metal compounds, such as phenyl-sodium, -potassium or -lithium or naphthalene-sodium, -potassium or -lithium. The reaction can also be carried out by converting the carbonyl compounds into their alkali or alkaline earth metal compounds and allowing these to react. in situ, with acetylene.

Alkaline catalysts, such as alkali or alkaline earth metal hydroxides, alcoholates or cabonates, for example, NaOH, KOH, NaOCH$_3$, KOCH$_3$, Na$_2$CO$_3$ or K$_2$CO$_3$, can be used in the reaction between compounds A—(p)—$C_6H_4$—CO—$R^1$ or A—O—(p)—$C_6H_4$—CO—$R^1$ and acetylene.

The reaction is carried out in inert solvents, for example, hydrocarbons, such as benzene, toluene or xylene, to which 0.5–5% by weight of oleic acid may be added, or with active solvents, including cyclic ethers, for example, THF or dioxane; dialkylamides with lower alkyl and acyl radicals, for example, DMF; ethers, such as diethyl, diisopropyl or di-tert.-butyl ether; pyridine and/or short-chain alcohols, such as methanol or ethanol, under reaction conditions given above.

Potassium hydroxide is preferably used as catalyst in ether in the presence of a trace of ethanol. The reaction is preferably done at 20° to 50° with an excess of KOH for relatively long reaction times, for example, 6-24 hours, under a slight excess pressure of acetylene, for example, 2-15 atmospheres, preferably about 8 atmospheres.

Reaction of compounds of formulae A—(p)—$C_6H_4$—CO—$R^1$ or A—O—(p)—$C_6H_4$—CO—$R^1$ with an alkali or alkaline earth metal acetylide, preferably with sodium or lithium acetylide as well as calcium or potassium acetylide, can also be carried out in liquid ammonia. One of the above inert solvents can be added. In this case, the reaction mixture is preferably kept saturated with acetylene. Temperatures between about −77° and −33° are required. The mixture is allowed to react from about 30 minutes to 48 hours, preferably between 1 and 14 hours. In some cases it is advisable to work under pressure of 1 to 50 atmospheres; the reaction temperature can then be higher, for example, between −30° and +30°.

In a further embodiment, compounds II (Q is OM; M is one equivalent of a heavy metal atom such as Ag, Cu or Hg) are also obtainable in situ by ethynylation of A—(p)—$C_6H_4$—CO—$R^1$ and A—O—(p)—$C_6H_4$—CO—$R^1$ in the presence of a catalyst, preferably in aqueous solution, under excess acetylene pressure at 50°-150°. Catalysts which can be used include acetylides of the metals of groups Ib and IIb of the periodic table, for example, copper or mercury acetylide, and addition compounds thereof with acetylene. These catalysts can be supported, as on finely divided SiO$_2$ or mixed therewith. Acetylene can be diluted with an inert gas, for example, N$_2$, typically in a ratio of 2:1. The reaction requires 20 minutes to 36 hours, preferably about 30 minutes to 6 hours.

Compounds of Formula II (Q is OM), can also be prepared from carbonyl compounds A—(p)—$C_6H_4$—CO—$R^1$ or A—O—(p)—$C_6H_4$—CO—$R^1$ and ethynyl magnesium halide under conditions customary for a Grignard synthesis, preferably in an inert solvent, such as an ether, for example, diethyl ether, diisopropyl ether, diethylene glycol diethyl ether or diethylene glycol dibutyl ether; a cyclic ether, for example, THF or dioxane; and/or carbon tetrachloride, at temperatures between about 0 and 70, preferably between 0° and 30°. Other metal acetylides M—C≡CH, for example, ethynyl zinc halides or ethynyl cadmium halides or silver acetylide can be used instead of ethynyl magnesium halide, under the same or similar reaction conditions.

Compounds of Formula II are also accessible by Grignard synthesis from carbonyl compounds of formulae A—(p)—$C_6H_4$—CO—C≡CH or A—O—(p)—$C_6H_4$—CO—C≡CH and an alkyl magnesium halide or from compounds of formula $R^1$—CO—C≡CH and a biphenylyl magnesium halide or a phenoxyphenyl magnesium halide of formulae A—(p)—$C_6H_4$—MgHal or A—O—(p)—$C_6H_4$—MgHal (Hal is Cl, Br or I) under the above reaction conditions. Corresponding lithium derivatives $R^1$Li, A—(p)—$C_6H_4$—Li or A—O—(p)—$C_6H_4$—Li can also be used for this reaction. The reaction is carried out under the same conditions as for the reaction with organomagnesium compounds.

Carbonyl compounds of formulae A—(p)—C$_6$H$_4$—CO—C≡CH or A—O—(p)—C$_6$H$_4$—CO—C≡CH can be prepared by reacting carboxylic acid halides A—(p)—C$_6$H$_4$—COX or A—O—(p)—C$_6$H$_4$—COX (X is Cl or Br) with silver acetylide or alkali metal acetylides in a solvent, for example, carbon tetrachloride. Carbonyl compounds R$^1$—CO—C≡CH are accessible analogously from carboxylic acid halides R$^1$COX.

Carbonyl compounds of formulae A—(p)—C$_6$H$_4$—CO—R$^1$ and A—O—(p)—C$_6$H$_4$—COR$^1$ are obtainable by Friedel-Crafts acylation of compounds of formulae A—C$_6$H$_5$ or A—O—C$_6$H$_5$ with acid chlorides of formula R$^1$COCl or, if R$^1$ is phenyl, by reaction of benzene with acid chlorides of formulae A—(p)—C$_6$H$_4$—COCl or A—O—(p)—C$_6$H$_4$—COCl in the presence of AlCl$_3$.

Metal acetylides M—C≡CH can be obtained according to known methods including reacting acetylene with an alkali metal, such as Li, Na or K; with an alkali metal hydride, such as LiH, NaH or KH; or with an alkali metal amide, such as LiNH$_2$, NaNH$_2$ or KNH$_2$, in an anhydrous solvent, such as dioxane, DMSO, THF and/or liquid ammonia.

In compounds of Formula II, Q can also be acyloxy, for example, alkanoyloxy, preferably of up to 7 carbon atoms, for example, acetoxy or enanthoyloxy, benzoyloxy or alkylsulfonyloxy or arylsulfonyloxy, wherein alkyl is of 1 to 6 carbon atoms and aryl is of 6 to 10 carbon atoms. Q is also alkoxy, preferably of up to 6 carbon atoms; aryloxy, preferably of 6 to 10 carbon atoms or aralkyloxy, preferably of 7 to 11 carbon atoms. Q can also be Cl, Br or I.

Compounds II in which Q is alkanoyloxy, benzoyloxy, alkylsulfonyloxy or arylsulfonyloxy are accessible by reacting compounds II (Q is Cl or Br) with alkali metal salts of the appropriate acids. Compounds II in which Q is alkoxy are obtained by reacting the same intermediates with appropriate alkali metal alcoholates. Compounds II (Q is I) are obtained by reacting compounds II (Q is Cl or Br) with potassium iodide in acetone.

Solvolysis of compounds of Formula II proceeds successfully in an acid, neutral or alkaline medium at temperatures between about −20° and 300°. Acid catalysts used are preferably HCl, H$_2$SO$_4$ or acetic acid or salts having an acidic reaction, such as ammonium chloride. Basic catalysts used include sodium hydroxide, potassium hydroxide, calcium hydroxide, sodium carbonate and potassium carbonate. Solvents are preferably water; lower alcohols, such as methanol or ethanol; ethers, such as THF or dioxane; amides, such as DMF; nitriles, such as acetonitrile; and/or sulfones, such as tetramethylenesulfone. Mixtures which contain water are preferred.

Metal alcoholates of Formula II (Q is OM), preferred starting materials, are generally not isolated but are hydrolyzed in situ, after their formation, with dilute acids, for example, sulfuric acid or hydrochloric acid, or with aqueous ammonium chloride solution, preferably at temperatures between 0° and 30°.

If desired, an alcohol of Formula I (R$^2$ is H) can be esterified with an organic carboxylic acid, for example, an alkanoic acid of up to 6 carbon atoms or an arylcarboxylic acid of up to 11 carbon atoms, or with a reactive derivative thereof, for example, a halide or anhydride, such as acetyl chloride, p-chlorobenzoic acid chloride, acetyl bromide or acetic anhydride. The esterification is preferably carried out in the presence of an acid or basic catalyst. Exemplary acid catalysts are inorganic or organic acids, such as HCl, HBr, HI, H$_2$SO$_4$, H$_3$PO$_4$, trifluoroacetic acid, benzenesulfonic acid or p-toluenesulfonic acid, or of an acid ion exchange resin. Basic catalysts are, for example, alkali metal hydroxides, such as NaOH or KOH; alkali metal carbonates, such as sodium carbonate or potassium carbonate; or organic bases, such as pyridine. An inert solvent, such as benzene, toluene or xylene, can be used. The reaction is done at temperatures between about 0° and about 140°, preferably between 20° and 100°.

The esterification is preferably carried out with an acid chloride or acid anhydride in pyridine at room temperature.

Alcohols I (R$^2$ is H) can also be esterified with ketenes. Formates I (R$^2$ is CHO) can preferably be obtained from alcohols I (R$^2$ is H) by heating with excess formic acid.

Compounds of Formula I can be converted by reaction with a base to a physiologically acceptable metal salt. These salts are, preferably, sodium, potassium, calcium, magnesium, copper(I) or copper(II) salts.

Compounds of Formula I can be liberated from metal salts thereof by treatment with acids or water.

Compounds of Formula I have a center of asymmetry and are usually in the racemic form. The racemates can be resolved into their optical antipodes by known mechanical or chemical methods.

It has been found that compounds of Formula I have valuable pharmacological properties and are well tolerated. Anti-inflammatory effects can be demonstrated on rats by the adjuvant-arthritis test of Newbould (Brit. J. Pharmacol., Volume 21, (1963), pages 127–136). Analgesic and antipyretic activity can be demonstrated by methods customary for this purpose. Lowering of the cholesterol level can be demonstrated by the method of Levine et al., Automation in Analytical Chemistry, Technicon Symposium 1967, Mediad, New York, pages 25–28, and lowering of triglyceride level by the method of Noble and Campbell, Clin. Chem., Volume 16, (1970), pages 166–170. Inhibition of thrombocyte aggregation is also observed.

Compounds of Formula I can be used as medicaments in human and veterinary medicine. They are also suitable as intermediates for the preparation of other medicaments.

Compounds of Formula I and/or, optionally, their physiologically acceptable metal salts can be used, mixed with solid, liquid and/or semi-liquid pharmaceutically acceptable excipients or carriers, as medicaments in human or veterinary medicine. Excipients which can be used are organic or inorganic substances which are suitable for enteral or parenteral administration or topical application and which do not react with the new compounds, for example, water, vegetable oils, benzyl alcohol, polyethylene glycols, gelatine, lactose, starch, magnesium stearate, talc, white petroleum jelly and cholesterol. Tablets, dragees, capsules, syrups, elixirs or suppositories are suitable for enteral administration. Formulations used for parenteral administration are, in particular, solutions, preferably oily or aqueous solutions, as well as suspensions, emulsions or implants. Those used for topical application are ointments, creams or powders.

The new compounds can also be lyophilized and the resulting lyophilizates can be used, for example, to prepare injection formulations. These formulations can be sterilized or contain auxiliaries, such as lubricants, preservatives, stabilizers and/or wetting agents, emulsifiers, salts for regulating osmotic pressure, buffer substances, dyestuffs, flavorings and/or aromatic substances. They can, if desired, also contain one or more other active compounds, for example, vitamins.

The compounds of Formula I are administered analogously to anti-inflammatory agents which are available commercially, such as indomethacin, preferably in dosages from about 5 to 500 mg., especially between 10 and 250 mg. per dosage unit. The daily dose is preferably between about 0.1 and 10 mg./kg. of body weight. However, the specific dose for each particular patient depends on diverse factors, for example, on the efficiency of the particular compound employed, on age, body weight, general state of health, sex, diet, time and route of administration, rate of excretion, the combination of medicinal substances being given the patient and on the severity of the particular illness to which the therapy is applied. Oral administration is preferred.

Each of the compounds on Formula I disclosed in the examples which follow is particularly suitable for the preparation of pharmaceutical formulations.

In the examples which follow "customary working up" means: water is added if necessary, the mixture is extracted with an organic solvent, such as benzene, chloroform or dichloromethane, the organic phase is separated off, dried over sodium sulfate, filtered and evaporated and the product is purified by chromatography and/or crystallization.

In the specification, text temperatures are given in degrees centigrade.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

A mixture of 0.84 g. of sodium hydride and 18 ml. of dry DMSO is heated to 70°–75° for 30 minutes under nitrogen. After cooling and adding 10 ml. of dry THF and a small amount of triphenylmethane indicator, acetylene is passed in until the red color disappears. A solution of 7.4 g. of 4'-fluoro-4-acetylbiphenyl, which can be prepared from 4-fluorobiphenyl and acetyl chloride in the presence of AlCl$_3$, in 20 ml. of THF and 7 ml. of DMSO is then added, while nitrogen is passed through the mixture. The resulting mixture, which contains sodium 3-(4'-fluoro-biphenylyl-4)-but-1-yn-3-olate, is hydrolyzed with an aqueous ammonium chloride solution and worked up in the customary manner to give 3-(4'-fluorobiphenylyl-4)-3-hydroxybutl-yne; m.p. 80°–82°.

EXAMPLES 2 to 46

By following the procedure of Example 1, the following compounds can be obtained from corresponding acetylbiphenylyl or acetyl-4-phenoxyphenyl compounds and sodium acetylide:

2. 3-(Biphenylyl-4)-3-hydroxybut-1-yne, m.p. 90°–92°.
3. 3-(2'-Fluorobiphenylyl-4)-3-hydroxybut-1-yne, m.p. 86°–88°.
4. 3-(3'-Fluorobiphenylyl-4)-3-hydroxybut-1-yne.
5. 3-(2'-Chlorobiphenylyl-4)-3-hydroxybut-1-yne.
6. 3-(3'-Chlorobiphenylyl-4)-3-hydroxybut-1-yne.
7. 3-(4'-Chlorobiphenylyl-4)-3-hydroxybut-1-yne, m.p. 106°–107°.
8. 3-(2'-Bromobiphenylyl-4)-3-hydroxybut-1-yne.
9. 3-(3'-Bromobiphenylyl-4)-3-hydroxybut-1-yne.
10. 3-(4'-Bromobiphenylyl-4)-3-hydroxybut-1-yne, m.p. 114°–116°.
11. 3-(2',3'-Difluorobiphenylyl-4)-3-hydroxybut-1-yne.
12. 3-(2',4'-Difluorobiphenylyl-4)-3-hydroxybut-1-yne, m.p. 64°–66°.
13. 3-(2',5'-Difluorobiphenylyl-4)-3-hydroxybut-1-yne.
14. 3-(2',6'-Difluorobiphenylyl-4)-3-hydroxybut-1-yne.
15. 3-(3',4'-Difluorobiphenylyl-4)-3-hydroxybut-1-yne.
16. 3-(3',5'-Difluorobiphenylyl-4)-3-hydroxybut-1-yne.
17. 3-(2',3'-Dichlorobiphenylyl-4)-3-hydroxybut-1-yne.
18. 3-(2',4'-Dichlorobiphenylyl-4)-3-hydroxybut-1-yne.
19. 3-(2',5'-Dichlorobiphenyl-4)-3-hydroxybut-1-yne.
20. 3-(2',6'-Dichlorobiphenylyl-4)-3-hydroxybut-1-yne.
21. 3-(3',4'-Dichlorobiphenylyl-4)-3-hydroxybut-1-yne.
22. 3-(3',5'-Dichlorobiphenylyl-4)-3-hydroxybut-1-yne.
23. 3-(2',4'-Dibromobiphenylyl-4)-3-hydroxybut-1-yne.
24. 3-(4-Phenoxyphenyl)-3-hydroxybut-1-yne.
25. 3-[4-(2-Fluorophenoxy)phenyl]-3-hydroxybut-1-yne.
26. 3-[4-(3-Fluorophenoxy)phenyl]-3-hydroxybut-1-yne.
27. 3-[4-(4-Fluorophenoxy)phenyl]-3-hydroxybut-1-yne, m.p. 54°–56°.
28. 3-[4-(2-Chlorophenoxy)phenyl]-3-hydroxybut-1-yne.
29. 3-[4-(3-Chlorophenoxy)phenyl]-3-hydroxybut-1-yne.
30. 3-[4-(4-Chlorophenoxy)phenyl]-hydroxybut-1-yne, m.p. 55°–57°.
31. 3-[4-(2-Bromophenoxy)phenyl]-3-hydroxybut-1-yne.
32. 3-[4-(3-Bromophenoxy)phenyl]-3-hydroxybut-1-yne.
33. 3-[4-(4-Bromophenoxy)phenyl]-3-hydroxybut-1-yne.
34. 3-[4-(2,3-Difluorophenoxy)phenyl]-3-hydroxybut-1-yne.
35. 3-[4-(2,4-Difluorophenoxy)phenyl]-3-hydroxybut-1-yne.
36. 3-[4-(2,5-Difluorophenoxy)phenyl]-3-hydroxybut-1-yne.
37. 3-[4-(2,6-Difluorophenoxy)phenyl]-3-hydroxybut-1-yne.
38. 3-[4-(3,4-Difluorophenoxy)phenyl]-3-hydroxybut-1-yne.
39. 3-[4-(3,5-Difluorophenoxy)phenyl]-3-hydroxybut-1-yne.
40. 3-[4-(2,3-Dichlorophenoxy)phenyl]-3-hydroxybut-1-yne.
41. 3-[4-(2,4-Dichlorophenoxy)phenyl]-3-hydroxybut-1-yne.
42. 3-[4-(2,5-Dichlorophenoxy)phenyl]-3-hydroxybut-1-yne.
43. 3-[4-(2,6-Dichlorophenoxy)phenyl]-3-hydroxybut-1-yne.
44. 3-[4-(3,4-Dichlorophenoxy)phenyl]-3-hydroxybut-1-yne.
45. 3-[4-(3,5-Dichlorophenoxy)phenyl]-3-hydroxybut-1-yne.
46. 3-[4-(2,4-Dibromophenoxy)phenyl]-3-hydroxybut-1-yne.

EXAMPLE 47

Analogously to Example 1, 3-(4'-fluorobiphenylyl-4)-3-hydroxypent-1-yne, m.p. 69°-71°, is obtained by reacting 8 g. of 4'-fluoro-4-propionylbiphenyl, which can be prepared from 4-fluorobiphenyl and propionyl chloride in the presence of $AlCl_3$, with sodium acetylide and subsequently hydrolyzing the reaction product.

EXAMPLES 48 to 116

Analogously to Example 47, the following alkyne compounds can be obtained from corresponding 1-formyl-, 1-propionyl-, 1-butyryl-, 1-pentanoyl- or 1-benzoyl-biphenylyl- or -(4-phenoxy)phenyl derivatives and sodium acetylide:

48. 3-(Biphenylyl-4)-3-hydroxypropyne.
49. 3-(2'-Flurobiphenylyl-4)-3-hydroxypropyne.
50. 3-(4'-Flurobiphenylyl-4)-3-hydroxypropyne.
51. 3-(2'-Chlorobiphenylyl-4)-3-hydroxypropyne.
52. 3-(4'-Chlorobiphenylyl-4)-3-hydroxypropyne.
53. 3-(4'-Bromobiphenylyl-4)-3-hydroxypropyne.
54. 3-(2',4'-Difluorobiphenylyl-4)-3-hydroxypropyne.
55. 3-(4-Phenoxyphenyl)-3-hydroxypropyne.
56. 3-[4-(2-Fluorophenoxy)phenyl]-3-hydroxypropyne.
57. 3-[4-(4-Fluorophenoxy)phenyl]-3-hydroxypropyne.
58. 3-[4-(2-Chlorophenoxy)phenyl]-3-hydroxypropyne.
59. 3-[4-(4-Chlorophenoxy)phenyl]-3-hydroxypropyne.
60. 3-[4-(4-Bromophenoxy)phenyl]-3-hydroxypropyne.
61. 3-[4-(2,4-Difluorophenoxy)phenyl]-3-hydroxypropyne.
62. 3-(Biphenylyl-4)-3-hydroxypent-1-yne.
63. 3-(2'-Fluorobiphenylyl-4)-3-hydroxypent-1-yne.
64. 3-(2'-Chlorobiphenylyl-4)-3-hydroxypent-1-yne.
65. 3-(4'-Chlorobiphenylyl-4)-3-hydroxypent-1-yne.
66. 3-(4'-Bromobiphenylyl-4)-3-hydroxypent-1-yne.
67. 3-(2',4'-Difluorobiphenylyl-4)-3-hydroxypent-1-yne.
68. 3-(4-Phenoxyphenyl)-3-hydroxypent-1-yne.
69. 3-[4-(2-Fluorophenoxy)phenyl]-3-hydroxypent-1-yne.
70. 3-[4-(4-Fluorophenoxy)phenyl]-3-hydroxypent-1-yne.
71. 3-[4-(2-Chlorophenoxy)phenyl]-3-hydroxypent-1-yne.
72. 3-[4-(4-Chlorophenoxy)phenyl]-3-hydroxypent-1-yne.
73. 3-[4-(4-Bromophenoxy)phenyl]-3-hydroxypent-1-yne.
74. 3-[4-(2,4-Difluorophenoxy)phenyl]-3-hydroxypent-1-yne.
75. 3-(Biphenylyl-4)-3-hydroxyhex-1-yne.
76. 3-(2'-Fluorobiphenylyl-4)-3-hydroxyhex-1-yne.
77. 3-(4'-Fluorobiphenylyl-4)-3-hydroxyhex-1-yne.
78. 3-(2'-Chlorobiphenylyl-4)-3-hydroxyhex-1-yne.
79. 3-(4'-Chlorobiphenylyl-4)-3-hydroxyhex-1-yne.
80. 3-(4'-Bromobiphenylyl-4)-3-hydroxyhex-1-yne.
81. 3-(2',4'-Difluorobiphenylyl-4)-3-hydroxyhex-1-yne.
82. 3-(4-Phenoxyphenyl)-3-hydroxyhex-1-yne.
83. 3-[4-(2-Fluorophenoxy)phenyl]-3-hydroxyhex-1-yne.
84. 3-[4-(4-Fluorophenoxy)phenyl]-3-hydroxyhex-1-yne.
85. 3-[4-(2-Chlorophenoxy)phenyl]-3-hydroxyhex-1-yne.
86. 3-[4-(4-Chlorophenoxy)phenyl]-3-hydroxyhex-1-yne.
87. 3-[4-(4-Bromophenoxy)phenyl]-3-hydroxyhex-1-yne.
88. 3-[4-(2,4-Difluorophenoxy)phenyl]-3-hydroxyhex-1-yne.
89. 3-(Biphenylyl-4)-3-hydroxyhept-1-yne.
90. 3-(2'-Fluorobiphenylyl-4)-3-hydroxyhept-1-yne.
91. 3-(4'-Fluorobiphenylyl-4)-3-hydroxyhept-1-yne, m.p. 61°-63°.
92. 3-(2'-Chlorobiphenylyl-4)-3-hydroxyhept-1-yne.
93. 3-(4'-Chlorobiphenylyl-4)-3-hydroxyhept-1-yne.
94. 3-(4'-Bromobiphenylyl-4)-3-hydroxyhept-1-yne.
95. 3-(2',4'-Difluorobiphenylyl-4)-3-hydroxyhept-1-yne.
96. 3-(4-Phenoxyphenyl)-3-hydroxyhept-1-yne.
97. 3-(4-(2-Fluorophenoxy)phenyl]-3-hydroxyhept-1-yne.
98. 3-[4-(4-Fluorophenoxy)phenyl]-3-hydroxyhept-1-yne, m.p. 61°-63°.
99. 3-[4-(2-Chlorophenoxy)phenyl]-3-hydroxyhept-1-yne.
100. 3-[4-(4-Chlorophenoxy)phenyl]-3-hydroxyhept-1-yne.
101. 3-[4-(4-Bromophenoxy)phenyl]-3-hydroxyhept-1-yne.
102. 3-[4-(2,4-Difluorophenoxy)phenyl]-3-hydroxyhept-1-yne.
103. 3-(Biphenylyl-4)-3-phenyl-3-hydroxypropyne.
104. 3-(2'-Fluorobiphenylyl-4)-3-phenyl-3-hydroxypropyne.
105. 3-(4'-Fluorobiphenylyl-4)-3-phenyl-3-hydroxypropyne, m.p. 95°-97°.
106. 3-(2'-Chlorobiphenylyl-4)-3-phenyl-3-hydroxypropyne.
107. 3-(4'-Chlorobiphenylyl-4)-3-phenyl-3-hydroxypropyne.
108. 3-(4'-Bromobiphenylyl-4)-3-phenyl-3-hydroxypropyne.
109. 3-(2',4'-Difluorobiphenylyl-4)-3-phenyl-3-hydroxypropyne.
110. 3-(4-Phenoxyphenyl)-3-phenyl-3-hydroxypropyne.
111. 3-[4-(2-Fluorophenoxy)phenyl]-3-phenyl-3-hydroxypropyne.
112. 3-[4-(4-Fluorophenoxy)phenyl]-3-phenyl-3-hydroxypropyne.
113. 3-[4-(2-Chlorophenoxy)phenyl]-3-phenyl-3-hydroxypropyne.
114. 3-[4-(4-Chlorophenoxy)phenyl]-3-phenyl-3-hydroxypropyne.
115. 3-[4-(4-Bromophenoxy)phenyl]-3-phenyl-3-hydroxypropyne.
116. 3-[4-(2,4-Difluorophenoxy)phenyl]-3-phenyl-3-hydroxypropyne.

EXAMPLE 117

214 g. of 4'-fluoro-4-acetylbiphenyl are added dropwise, over 3 hours, to a solution of sodium acetylide, prepared from 25 g. of sodium, in 600 ml. of liquid ammonia. The mixture is stirred for 150 minutes at −35°. 65 g. of ammonium chloride are then added to the solution, which contains sodium 3-(4'-fluorobiphenylyl-4)-but-1-yn-3-olate. Ammonia is evaporated off over about 12 hours. After the customary work up, 3-(4'-fluorobiphenylyl-4)-3-hydroxybut-1-yne, m.p. 80°-82°, is obtained.

EXAMPLE 118

8.34 g. of lithium are added at −70°, over three hours, to 900 ml. of liquid ammonia saturated with acetylene. When the blue color has disappeared, 214 g. of 4'-fluoro-4-acetylbiphenyl in 200 ml. of ether are added over one hour while acetylene is passed into the mixture. Ammonia is allowed to evaporate from the solution, which contains lithium 3-(4'-fluorobiphenylyl-4)-but-1-yn-3-olate, at +25°. Simultaneously, ether is added so that the volume of the mixture remains approximately constant. After the ammonia has been removed, no further acetylene is added while the mixture is allowed to stand for 12 hours at 20°. The reaction product is then hydrolyzed with 150 ml. of water and the ether layer is worked up in the customary manner to give 3-(4'-fluorobiphenylyl-4)-3-hydroxybut-1-yne, m.p. 80°–82°.

EXAMPLE 119

A solution of 2.47 g. of 4'-chloro-4-acetyldiphenyl ether, which can be prepared from 4-chlorodiphenyl ether and acetyl chloride in the presence of AlCl$_3$, in 6 ml. of THF and 2 ml. of DMSO is added dropwise to a suspension of 1.38 g. of lithium acetylide/ethylenediamine complex in a mixture of 3 ml. of absolute THF and 4 ml. of absolute DMSO, while acetylene is bubbled through the mixture. The mixture is stirred for one hour while under nitrogen blanketing. An aqueous solution of ammonium chloride is added to the solution, which contains lithium 3-[4-(4-chlorophenoxy)phenyl]-but-1-yn-3-olate and the mixture is poured into water and worked up in the customary manner to give 3-[4-(4-chlorophenoxy)phenyl]-3-hydroxybut-1-yne, m.p. 55°–57°.

EXAMLE 120

An acetylene-magnesium bromide solution is prepared from 8 g. of magnesium, 52.5 g. of bromobenzene and acetylene. To this is added, with stirring and cooling, 71 g. of 4'-fluoro4-acetylbiphenyl in 200 ml. of ether. The solution is allowed to stand for 3 days at 20°. Ice water is then added to hydrolyze the 3-(4'-fluorobiphenylyl-4)-but-1-ynyl-3-oxy-magnesium bromide. The mixture is then acidified with dilute sulfuric acid and extracted with ether. After drying over sodium sulfate and removing the solvent, 3-(4'-fluorobiphenylyl-4)-3-hydroxybut-1-yne is obtained, m.p. 80°–82°.

EXAMPLE 121

A solution of 22.4 g. of (4'-fluorobiphenylyl-4)-ethynyl ketone, which can be prepared from 3-(4'-fluorobiphenylyl-4)-3-hydroxyprop-1-yne by oxidation with chromium trioxide/sulfuric acid in water/acetone, in 100 ml. of absolute diethyl ether is added dropwise to a Grignard solution, cooled to 0°, prepared from 5.3 g. of magnesium and 31.2 g. of methyl iodide in 200 ml. of diethyl ether. The temperature of the stirred mixture is allowed to rise to 20°, and the solution containing 3-(4'-fluorobiphenylyl-4)-but-1-yn-3-yloxy-magnesium iodide is hydrolyzed with an aqueous solution of ammonium chloride in the customary manner. 3-(4'-Fluorobiphenyl-4)-3-hydroxybut-1-yne, m.p. 80°–82°, is obtained.

EXAMPLE 122

A solution of 6.8 g. of acetylacetylene in 50 ml. of diethyl ether is added, at 0°, to a solution of 70 g. of 4'-fluorobiphenylyl-4-magnesium iodide, which can be prepared by nitrating 4-fluorobiphenyl, reducing the resulting 4'-fluoro-4-nitrobiphenyl to the amine, converting the latter to 4'-fluoro-4-iodobiphenyl by a Sandmeyer reaction and reacting the product with magnesium, in 400 ml. of diethyl ether. The temperature of the stirred solution is allowed to rise to 20° and the solution is stirred at 20° for 2 hours more. An aqueous solution of ammonium chloride is then added to hydrolyze the 3-(4'-fluorobiphenylyl-4)-but-1-yn-3-yloxy-magnesium bromide and the product is worked up in the customary manner. 3-(4'-Fluorobiphenylyl-4)-3-hydroxybut-1-yne melts at 80°–82°.

EXAMPLE 123

A solution of 6.8 g. of acetylacetylene in 50 ml. of diethyl ether is added, at 0°, to a solution of 35 g. of 4-lithium-4'-fluorobiphenyl, which can be prepared by brominating 4-fluorobiphenyl and subsequently reacting the product with lithium, in 200 ml. of diethyl ether. After warming to 20°, the solution is heated under reflux for 2 hours, and an aqueous solution of ammonium chloride is added to hydrolyze the lithium 3-(4'-fluorobiphenylyl-4)-but-1-yn-3-olate. The product is then worked up in the customary manner. This gives 3-(4'-fluorobiphenylyl-4)-3-hydroxybut-1-yne, m.p. 80°–82°.

EXAMPLE 124

A mixture of 5 g. of 3-(4'-fluorobiphenylyl-4)-3-hydroxybut-1-yne, 25 ml. of acetic anhydride and 25 ml. of pyridine is heated to 60° for 20 hours. The reaction mixture is poured into water and worked up in the customary manner to give 3-(4'-fluorobiphenylyl-4)-3-acetoxybut-1-yne, m.p. 103°–104°.

EXAMPLES 125 to 196

Analogously to Example 124, the following compounds of Formula I can be obtained by acylating the corresponding 3-biphenylyl- and 3-(4-phenoxyphenyl)-3-hydroxyprop-1-yne, -but-1-yne, -pent-1-yne, -hex-1-yne and -hept-1-yne compounds:

125. 3-(Biphenylyl-4)-3-acetoxybut-1-yne.
126. 3-(2'-Fluorobiphenylyl-4)-3-acetoxybut-1-yne, m.p. 66°–68°.
127. 3-(3'-Fluorobiphenylyl-4)-3-acetoxybut-1-yne.
128. 3-(4'-Bromobiphenylyl-4)-3-acetoxybut-1-yne, m.p. 121°–123°.
129. 3-(2',4'-Difluorobiphenyl-4)-3-acetoxybut-1-yne, m.p. 99°–101°.
130. 3-(3',4'-Difluorobiphenylyl-4)-3-acetoxybut-1-yne.
131. 3-(3',5'-Difluorobiphenyl-4)-3-acetoxybut-1-yne.
132. 3-(2',4'-Dichlorobiphenylyl-4)-3-acetoxybut-1-yne.
133. 3-(2',4'-Dibromobiphenylyl-4)-3-acetoxybut-1-yne.
134. 3-(4-Phenoxyphenyl)-3-acetoxybut-1-yne.
135. 3-[4-(2-Fluorophenoxy)phenyl]-3-acetoxybut-1-yne.
136. 3-[4-(3-Fluorophenoxy)phenyl]-3-acetoxybut-1-yne.
137. 3-[4-(4-Fluorophenoxy)phenyl]-3-acetoxybut-1-yne.
138. 3-[4-(4-Chlorophenoxy)phenyl]-3-acetoxybut-1-yne.
139. 3-[4-(4-Bromophenoxy)phenyl]-3-acetoxybut-1-yne.
140. 3-[4-(2,4-Difluorophenoxy)phenyl]-3-acetoxybut-1-yne.
141. 3-[4-(2,4-Dichlorophenoxy)phenyl]-3-acetoxybut-1-yne.
142. 3-[4-(2,4-Dibromophenoxy)phenyl]-3-acetoxybut-1-yne.
143. 3-(Biphenylyl-4)-3-acetoxypropyne.
144. 3-(4'-Fluorobiphenylyl-4)-3-acetoxypropyne.
145. 3-(2',4'-Difluorobiphenylyl-4)-3-acetoxypropyne.
146. 3-(4-Phenoxyphenyl)-3-acetoxypropyne.

147. 3-[4-(4-Fluorophenoxy)phenyl]-3-acetoxypropyne.
148. 3-[4-(2,4-Difluorophenoxy)phenyl]-3-acetoxypropyne.
149. 3-(Biphenylyl-4)-3-acetoxypent-1-yne.
150. 3-(4'-Fluorobiphenylyl-4)-3-acetoxypent-1-yne.
151. 3-(2',4'-Difluorobiphenylyl-4)-3-acetoxypent-1-yne.
152. 3-(4-Phenoxyphenyl)-3-acetoxypent-1-yne.
153. 3-[4-(4-Fluorophenoxy)phenyl]-3-acetoxypent-1-yne.
154. 3-[4-(2,4-Difluorophenoxy)phenyl]-3-acetoxypent-1-yne.
155. 3-(Biphenylyl-4)-3-acetoxyhex-1-yne.
156. 3-(4'-Fluorobiphenylyl-4)-3-acetoxyhex-1-yne.
157. 3-(2',4'-Difluorobiphenylyl-4)-3-acetoxyhex-1-yne.
158. 3-(4-Phenoxyphenyl)-3-acetoxyhex-1-yne.
159. 3-[4-(4-Fluorophenoxy)phenyl]-3acetoxyhex-1-yne.
160. 3-[4-(2,4-Difluorophenoxy)phenyl]-3-acetoxyhex-1-yne.
161. 3-(Biphenyl-4)-3-acetoxyhept-1-yne.
162. 3-(4'-Fluorobiphenylyl-4)-3-acetoxyhept-1-yne.
163. 3-(2',4'-Difluorobiphenylyl-4)-3-acetoxyhept-1-yne.
164. 3-(4-Phenoxyphenyl)-3-acetoxyhept-1-yne.
165. 3-[4-(4-Fluorophenoxy)phenyl]-3-acetoxyhept-1-yne.
166. 3-[4-(2,4-Difluorophenoxy)phenyl]-3-acetoxyhept-1-yne.
167. 3-(Biphenylyl-4)-3-phenyl-3-acetoxypropyne.
168. 3-(4-Fluorobiphenylyl-4)-3-phenyl-3-acetoxypropyne.
169. 3-(2',4'-Difluorobiphenylyl-4)-3-phenyl-3-acetoxypropyne.
170. 3-(4-Phenoxyphenyl)-3-phenyl-3-acetoxypropyne.
171. 3-[4-84-Fluorophenoxy)phenyl]-3-phenyl-3-acetoxypropyne.
172. 3-[4-(2,4-Difluorophenoxy)phenyl]-3-phenyl-3-acetoxypropyne.
173. 3-(4'-Fluorobiphenyl-4)-3-formyloxybut-1-yne.
174. 3-(4'-Flurobiphenylyl-4)-3-propionyloxybut-1-yne.
175. 3-(4'-Fluorobiphenylyl-4)-3-butyryloxybut-1-yne.
176. 3-(Biphenylyl-4)-3-pivaloyloxybut-1-yne.
177. 3-(4'-Fluorobiphenylyl-4)-3-pivaloyloxypropyne.
178. 3-(4'-Fluorobiphenylyl-4l )-3-pivaloyloxybut-1-yne.
179. 3-(4'-Fluorobiphenylyl-4)-3-pivaloyloxypent-1-yne.
180. 3-(4'-Fluorobiphenylyl-4)-3-pivaloyloxyhex-1-yne.
181. 3-(4'-Fluorobiphenylyl-4)-3-pivaloyloxyhept-1-yne.
182. 3-(4'-Fluorobiphenylyl-4)-3-phenyl-3-pivaloyloxypropyne.
183. 3-(4'-Fluorobiphenylyl-4)-3-hexanoyloxybut-1-yne.
184. 3-(4'-Fluorobiphenylyl-4)-3-benzoyloxybut-1-yne.
185. 3-[4-(4-Fluorophenoxy)phenyl]-3-formyloxybut-1-yne.
186. 3-[4-(4-Fluorophenoxy)phenyl]-3-propionyloxybut-1-yne.
187. 3-[4-(4-Fluorophenoxy)phenyl]-3-butyryloxybut-1-yne.
188. 3-(4-Phenoxyphenyl)-3-pivaloyloxybutyne.
189. 3-[4-(4-Fluorophenoxy)phenyl]-3-pivaloyloxypropyne.
190. 3-[4-(4-Fluorophenoxy)phenyl]-3-pivaloyloxybut-1-yne.
191. 3-[4-(4-Fluorophenoxy)phenyl]-3-pivaloyloxypent-1-yne.
192. 3-[4-(4-Fluorophenoxy)phenyl]-3-pivaloyloxyhex-1-yne.
193. 3-[4-(4-Fluorophenoxy)phenyl]-3-pivaloyloxyhept-1-yne.
194. 3-[4-(4-Fluorophenoxy)phenyl]-3-phenyl-3-pivaloyloxypropyne.
195. 3-[4-(4-Fluorophenoxy)phenyl]-3-hexanoyloxybut-1-yne.
196. 3-[4-(4-Fluorophenoxy)phenyl]-3-benzoyloxybut-1-yne.

EXAMPLE 197

A mixture of 1 g. of 3-(4'-fluorobiphenylyl-4)-3-hydroxybutyne in 20 ml. of aqueous ethanol (20% water) is shaken vigorously with an excess of an ammoniacal copper (I) chloride solution and the precipitate is filtered off to give the copper (I) salt of 3-(4'-fluorobiphenylyl-4)-3-hydroxybutyne, an amorphous powder.

Examples given below related to pharmaceutical formulations which contain active compounds of Formula I or their physiologically acceptable salts.

Example A: Tablets

A mixture of 1 kg. of 3-(4'-fluorobiphenylyl-4)-3-hydroxybut-1-yne, 4 kg. of lactose, 1.2 kg. of potato starch, 0.2 kg. of talc and 0.1 kg. of magnesium stearate is pressed in the customary manner to give tablets each of which contains 100 mg. of active compound.

Example B: Dragees

Tablets are pressed analogously to Example A and subsequently coated in the customary manner with a coating consisting of sugar, maize starch, talc and tragacanth.

Examples C: Capsules 5 kg. of 3-(4'-fluorobiphenylyl-4)-3-hydroxybut-1-yne are filled into hard gelatine capsules in the customary manner so that each capsule contains 250 mg. of active compounds.

Tablets, dragees and capsules which contain one or more of the other active compounds of Formula I or of their physiologically acceptable salts are obtainable analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

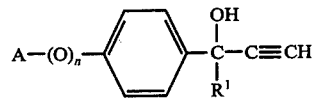

wherein $R^1$ is alkyl of up to 4 carbon atoms; A is monohaloor dihalophenyl wherein halo is F, Cl or Br and n is 0 or 1, and physiologically acceptable metal salts thereof.

2. A compound of claim 1, wherein $n$ is 0.

3. A compound of claim 1, wherein $n$ is 1.

4. A compound of claim 1, wherein $R^1$ is $CH_3$.

5. A compound of claim 1, wherein A is, fluorophenyl or difluorophenyl.

6. A compound of claim 1, wherein A is, oor p-fluorophenyl or 2,4-difluorophenyl.

7. A compound of claim 1, wherein A is, o- or p-fluorophenyl, p-chlorophenyl or 2,4-difluorophenyl; $R^1$ is methyl; and $n$ is 0.

8. A compound of claim 1, wherein A is o- or p-fluorophenyl, p-chlorophenyl or 2,4-difluorophenyl; $R^1$ is methyl; and $n$ is 1.

9. 3-(2'-Fluorobiphenylyl-4)-3-hydroxybut-1-yne, a compound of claim 1.

10. 3-(4'-Fluorobiphenylyl-4)-3-hydroxybut-1-yne, a compound of claim 1.

11. 3-(2',4'-Difluorobiphenylyl-4)-3-hydroxybut-1-yne, a compound of claim 1.

12. 3-(4'-Chlorobiphenylyl-4)-3-hydroxybut-1-yne, a compound of claim 1.

13. 3-(4'-Bromobiphenylyl-4)-3-hydroxybut-1-yne, a compound of claim 1.

14. 3-[4-(4-Fluorophenoxy)phenyl]-3-hydroxybut-1-yne, a compound of claim 1.

15. 3-[4-(4-Chlorophenoxy)phenyl]-3-hydroxybut-1-yne, a compound of claim 1.

16. 3-(4'-Fluorobiphenylyl-4)-3-hydroxypent-1-yne, a compound of claim 1.

17. 3-(4'-Fluorobiphenylyl-4)-3-hydroxyhept-1-yne, a compound of claim 1.

18. 3-[4-(4-Fluorophenoxy)phenyl]-3-hydroxyhept-1-yne, a compound of claim 1.

19. An anti-inflammatory pharmaceutical composition, comprising an anti-inflammatorily effective amount per unit dosage of a compound of claim 1, in admixture with a pharmaceutically acceptable carrier.

20. A method of treating an animal afflicted with an inflammatory condition, comprising administering to the afflicted animal an anti-inflammatorily effective amount of a compound of claim 1, in admixture with a pharmaceutically acceptable carrier.

21. The method of claim 20, wherein the compound is 3-(4'-fluorobiphenylyl)-3-hydroxybut-1-yne.

22. The method of claim 20, wherein the administration is oral.

23. A composition according to claim 19, adapted for oral administration.

24. A composition according to claim 23, in the form of a tablet, dragee or capsule.

* * * * *